(12) United States Patent
Lins

(10) Patent No.: US 8,123,783 B2
(45) Date of Patent: Feb. 28, 2012

(54) PEDICLE SCREW-BASED DYNAMIC POSTERIOR STABILIZATION SYSTEMS AND METHODS

(75) Inventor: Robert E. Lins, Boca Raton, FL (US)

(73) Assignee: US Spine, Inc., Salt Lake City, UT (US)

( * ) Notice: Subject to any disclaimer, the term of this patent is extended or adjusted under 35 U.S.C. 154(b) by 563 days.

(21) Appl. No.: 11/418,640

(22) Filed: May 5, 2006

(65) Prior Publication Data

US 2006/0264941 A1    Nov. 23, 2006

Related U.S. Application Data

(60) Provisional application No. 60/678,638, filed on May 6, 2005.

(51) Int. Cl.
| | |
|---|---|
| A61B 17/70 | (2006.01) |
| A61B 17/04 | (2006.01) |
| A61B 17/86 | (2006.01) |
| A61B 17/56 | (2006.01) |
| A61B 17/58 | (2006.01) |
| A61B 17/80 | (2006.01) |
| A61F 2/08 | (2006.01) |
| A61F 2/30 | (2006.01) |
| F16C 11/00 | (2006.01) |

(52) U.S. Cl. .......... 606/257; 606/71; 606/308; 403/123; 403/124; 403/125

(58) Field of Classification Search ................ 606/257, 606/71, 308, 256, 259, 260, 261, 305, 307, 606/320; 464/32, 55, 97, 98, 110, 161, 169, 464/171; 403/57, 63, 80, 82, 114, 123, 124, 403/125, 132, 142, 145, 157, 165, 166, 223, 403/233, 234, 235, 237, 241
See application file for complete search history.

(56) References Cited

U.S. PATENT DOCUMENTS

| | | | | |
|---|---|---|---|---|
| 5,961,516 | A | * 10/1999 | Graf | 606/256 |
| 6,248,106 | B1 | * 6/2001 | Ferree | 606/263 |
| 2005/0203519 | A1 | * 9/2005 | Harms et al. | 606/61 |
| 2006/0084984 | A1 | * 4/2006 | Kim | 606/61 |

FOREIGN PATENT DOCUMENTS

| | | | |
|---|---|---|---|
| DE | 102004011685.7 | * | 3/2004 |
| EP | 669109 A1 | * | 8/1995 |

OTHER PUBLICATIONS

Web Page: Dynesys Dynamic Stabilization System; Zimmer Spine, Minnesota USA.

* cited by examiner

*Primary Examiner* — Thomas C Barrett
*Assistant Examiner* — David Bates
(74) *Attorney, Agent, or Firm* — Stoel Rives LLP; Matthew D. Thayne

(57) ABSTRACT

The present invention provides a pedicle screw-based dynamic posterior stabilization system that is used to stabilize the segments of the cervical, thoracic, lumbar, and sacral spine as an adjunct to, or in place of, conventional spinal fusion using bone grafts. The system includes a plurality of pedicle screws, each of the plurality of pedicle screws including a head portion, and the head portion of each of the plurality of pedicle screws forming a first half of a joint that allows relative pivoting movement about the head portion of each of the plurality of pedicle screws and up-and-down movement with respect to the head portion of each of the plurality of pedicle screws. The system also includes a stabilization body coupled to the plurality of pedicle screws, the stabilization body including a plurality of end portions, and the end portions of the stabilization body forming a plurality of second halves of the joints formed by the head portion of each of the plurality of pedicle screws.

22 Claims, 5 Drawing Sheets

PEDICLE SCREW-BASED DYNAMIC POSTERIOR STABILIZATION SYSTEMS AND METHODS

CROSS-REFERENCE TO RELATED APPLICATION(S)

The present non-provisional patent application claims the benefit of priority of U.S. Provisional Patent Application No. 60/678,638, filed on May 6, 2005, and entitled "PEDICLE SCREW-BASED DYNAMIC POSTERIOR STABILIZATION SYSTEMS AND METHODS." The contents of this provisional patent application are incorporated in full by reference herein.

FIELD OF THE INVENTION

The present invention relates generally to the medical device and surgical fields. More specifically, the present invention relates to improved pedicle screw-based dynamic posterior stabilization systems and methods that are used to stabilize the segments of the cervical, thoracic, lumbar, and sacral spine as an adjunct to, or in place of, conventional spinal fusion using bone grafts—formerly also using fusion cages, various pedicle screws, and/or rigid rods. The pedicle screw-based dynamic posterior stabilization systems and methods of the present invention are used in the treatment of degenerative spondylolisthesis, degenerative disc disease, lumbar spinal stenosis, and the like.

BACKGROUND OF THE INVENTION

The spine is a complex columnar structure that is comprised of vertebral bone and connective tissues. The vertebrae, intervertebral discs, and ligaments are intricately arranged such that the interaction between these structures provides strength and support for the distribution of body forces and flexibility for body motion, as well as protection for the spinal cord. In a diseased or injured spine, this intricate arrangement is disrupted. In many cases, such disruptions can be treated by conservative, non-surgical methods, such as medication, exercise, physical therapy, etc. In some cases, however, more radical, surgical methods are required to treat the pain and other symptoms caused by nerve element compression and unstable intervertebral joints. Such more radical, surgical methods involve the dissection of soft tissue and often the removal of load-bearing structures, such as vertebral bone and intervertebral discs. This can lead to spinal instability, and it is often necessary to fuse the associated segments (also referred to as levels) in order to restore spinal stability. Internal fixation with instrumentation typically accompanies spinal fusion to provide temporary spinal stabilization and alignment, as well as an environment in which fusion can take place over time.

A variety of internal fixation systems have been developed to provide temporary spinal stabilization and alignment. These internal fixation systems can be defined as anterior or posterior assemblies, depending on how and where they are implanted with respect to the spine. Anterior assemblies, such as total intervertebral disc replacement assemblies and the like, are coupled to the anterior (front) portion of the spine, while posterior assemblies are coupled to the posterior (rear) portion of the spine, using various pedicle screws and rigid rods, for example. These posterior assemblies typically include adjacent pairs of screws that are inserted through the pedicles and into the vertebral bodies at predetermined angles and depths. Pairs of parallel, longitudinally-aligned rigid rods are then disposed through and/or attached to the adjacent pairs of pedicle screws, essentially creating an immobilizing frame or support structure. Disadvantageously, although providing temporary spinal stabilization and alignment, these internal fixation systems often require an open posterior insertion procedure with a typical incision and muscle retraction, destroy significant portions of the pedicles (facets), result in an undesirably limited range of motion (ROM), are difficult to revise and/or extract, and can lead to adjacent-level degenerative disc disease.

One conventional system for the stabilization of the segments of the cervical, thoracic, lumbar, and sacral spine as an adjunct to conventional spinal fusion (incorporating autogenous bone grafts only)—formerly also using fusion cages, various pedicle screws, and/or rigid rods—is the Dynesys® Dynamic Stabilization System (Zimmer Spine, Minneapolis, Minn. USA). This system uses a plurality of titanium alloy pedicle screws (disposed lateral to the facets of adjacent vertebrae, on either side of the facets) through which a pair of parallel, flexible polyethylene terepthalate (PET) cords are threaded, the cords secured to the plurality of pedicle screws subsequent to proper sizing. A pair of flexible polycarbonate urethane (PCU) spacers are disposed about the cords. The push-pull interaction between the cords and the spacers stabilizes the intervertebral segment. In addition, the tension of the cords decreases post-operatively, due to body temperature warming, repetitive deformation, etc., resulting in a controlled increase in ROM. Advantageously, the system allows for an open posterior insertion procedure with a typical incision and muscle retraction or a minimally-invasive insertion procedure, preserves significant portions of the pedicles (facets), and results in an improved ROM (at rest, in flexion, and in extension). Disadvantageoulsy, the system is difficult to revise if the pedicle screws become loose.

Thus, what are still needed in the art are improved pedicle screw-based dynamic posterior stabilization systems and methods that are used to stabilize the segments of the cervical, thoracic, lumbar, and sacral spine as an adjunct to, or in place of, conventional spinal fusion using bone grafts—formerly also using fusion cages, various pedicle screws, and/or rigid rods. Advantageously, the pedicle screw-based dynamic posterior stabilization systems and methods of the present invention have a more physiologic dynamic interface that allows for more "normal" spine motion, as well as a decreased incidence of pedicle screw loosening.

BRIEF SUMMARY OF THE INVENTION

In various exemplary embodiments, the present invention provides improved pedicle screw-based dynamic posterior stabilization systems and methods that are used to stabilize the segments of the cervical, thoracic, lumbar, and sacral spine as an adjunct to, or in place of, conventional spinal fusion using bone grafts—formerly also using fusion cages, various pedicle screws, and/or rigid rods. The pedicle screw-based dynamic posterior stabilization systems and methods of the present invention are used in the treatment of degenerative spondylolisthesis, degenerative disc disease, lumbar spinal stenosis, and the like. Advantageously, the pedicle screw-based dynamic posterior stabilization systems and methods of the present invention have a more physiologic dynamic interface that allows for more "normal" spine motion, as well as a decreased incidence of pedicle screw loosening.

In one exemplary embodiment of the present invention, a pedicle screw-based dynamic posterior stabilization system that is used to stabilize the segments of the cervical, thoracic, lumbar, and sacral spine as an adjunct to, or in place of, conventional spinal fusion using bone grafts includes a plurality of pedicle screws, each of the plurality of pedicle screws including a head portion, and the head portion of each of the plurality of pedicle screws forming a first half of a joint that allows relative pivoting movement about the head portion of each of the plurality of pedicle screws and up-and-down movement with respect to the head portion of each of the plurality of pedicle screws. The system also includes a stabilization body coupled to the plurality of pedicle screws, the stabilization body including a plurality of end portions, and the end portions of the stabilization body forming a plurality of second halves of the joints formed by the head portion of each of the plurality of pedicle screws. Preferably, the head portion of each of the plurality of pedicle screws defines at least one hollow channel. Preferably, the stabilization body also defines at least one hollow channel. The system further includes a band that is threaded through the at least one hollow channel defined by the head portion of each of the plurality of pedicle screws and the at least one hollow channel defined by the stabilization body, the band selectively coupling the stabilization body to the plurality of pedicle screws. Preferably, the joints formed by the head portion of each of the plurality of pedicle screws comprise "double-saddle" joints.

In another exemplary embodiment of the present invention, a pedicle screw-based dynamic posterior stabilization method that is used to stabilize the segments of the cervical, thoracic, lumbar, and sacral spine as an adjunct to, or in place of, conventional spinal fusion using bone grafts includes inserting a plurality of pedicle screws in the facets of a plurality of adjacent vertebrae of a spine, each of the plurality of pedicle screws including a head portion, and the head portion of each of the plurality of pedicle screws forming a first half of a joint that allows relative pivoting movement about the head portion of each of the plurality of pedicle screws and up-and-down movement with respect to the head portion of each of the plurality of pedicle screws. The method also includes disposing a stabilization body between and coupling the stabilization body to the plurality of pedicle screws, the stabilization body including a plurality of end portions, and the end portions of the stabilization body forming a plurality of second halves of the joints formed by the head portion of each of the plurality of pedicle screws. Preferably, the head portion of each of the plurality of pedicle screws defines at least one hollow channel. Preferably, the stabilization body also defines at least one hollow channel. The method further includes threading a band through the at least one hollow channel defined by the head portion of each of the plurality of pedicle screws and the at least one hollow channel defined by the stabilization body, the band selectively coupling the stabilization body to the plurality of pedicle screws. Preferably, the joints formed by the head portion of each of the plurality of pedicle screws comprise "double-saddle" joints.

In a further exemplary embodiment of the present invention, a pedicle screw-based dynamic posterior stabilization system that is used to stabilize the segments of the cervical, thoracic, lumbar, and sacral spine as an adjunct to, or in place of, conventional spinal fusion using bone grafts includes a plurality of pedicle screws, each of the plurality of pedicle screws including a head portion, and the head portion of each of the plurality of pedicle screws forming a first half of a joint that allows relative pivoting movement about the head portion of each of the plurality of pedicle screws and up-and-down movement with respect to the head portion of each of the plurality of pedicle screws. The system also includes a stabilization body coupled to the plurality of pedicle screws, the stabilization body including a plurality of end portions, and the end portions of the stabilization body forming a plurality of second halves of the joints formed by the head portion of each of the plurality of pedicle screws. Preferably, the stabilization body defines at least one hollow channel. The system further includes a band that is threaded about the head portion of each of the plurality of pedicle screws and through the at least one hollow channel defined by the stabilization body, the band selectively coupling the stabilization body to the plurality of pedicle screws. Preferably, the joints formed by the head portion of each of the plurality of pedicle screws comprise "double-saddle" joints.

In a still further exemplary embodiment of the present invention, a pedicle screw-based dynamic posterior stabilization method that is used to stabilize the segments of the cervical, thoracic, lumbar, and sacral spine as an adjunct to, or in place of, conventional spinal fusion using bone grafts includes inserting a plurality of pedicle screws in the facets of a plurality of adjacent vertebrae of a spine, each of the plurality of pedicle screws including a head portion, and the head portion of each of the plurality of pedicle screws forming a first half of a joint that allows relative pivoting movement about the head portion of each of the plurality of pedicle screws and up-and-down movement with respect to the head portion of each of the plurality of pedicle screws. The method also includes disposing a stabilization body between and coupling the stabilization body to the plurality of pedicle screws, the stabilization body including a plurality of end portions, and the end portions of the stabilization body forming a plurality of second halves of the joints formed by the head portion of each of the plurality of pedicle screws. Preferably, the stabilization body defines at least one hollow channel. The method further includes threading a band about the head portion of each of the plurality of pedicle screws and through the at least one hollow channel defined by the stabilization body, the band selectively coupling the stabilization body to the plurality of pedicle screws. Preferably, the joints formed by the head portion of each of the plurality of pedicle screws comprise "double-saddle" joints.

BRIEF DESCRIPTION OF THE DRAWINGS

The present invention is illustrated and described herein with reference to the various drawings, in which like reference numbers denote like system components and/or method steps, as appropriate, and in which.

DETAILED DESCRIPTION OF THE INVENTION

In various exemplary embodiments, the present invention provides improved pedicle screw-based dynamic posterior stabilization systems and methods that are used to stabilize the segments of the cervical, thoracic, lumbar, and sacral spine as an adjunct to, or in place of, conventional spinal fusion using bone grafts—formerly also using fusion cages, various pedicle screws, and/or rigid rods. The pedicle screw-based dynamic posterior stabilization systems and methods of the present invention are used in the treatment of degenerative spondylolisthesis, degenerative disc disease, lumbar spinal stenosis, and the like. Advantageously, the pedicle screw-based dynamic posterior stabilization systems and methods of the present invention have a more physiologic dynamic interface that allows for more "normal" spine motion, as well as a decreased incidence of pedicle screw loosening.

Figure 1:
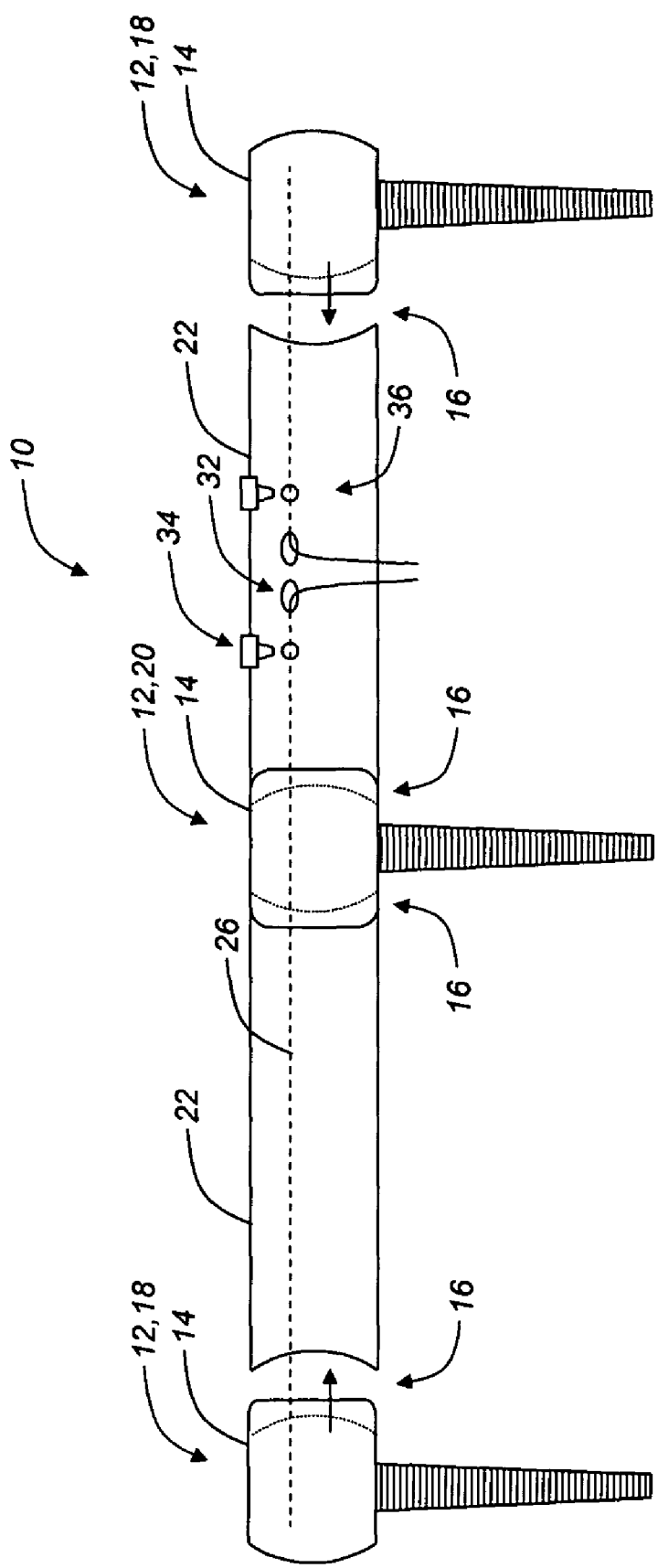
FIG. 1 is a side planar view illustrating one exemplary (multi-segment) embodiment of the pedicle screw-based dynamic posterior stabilization system of the present invention, the pedicle screw end portions being partially exploded from the stabilization bodies for clarity.
Figure 2:
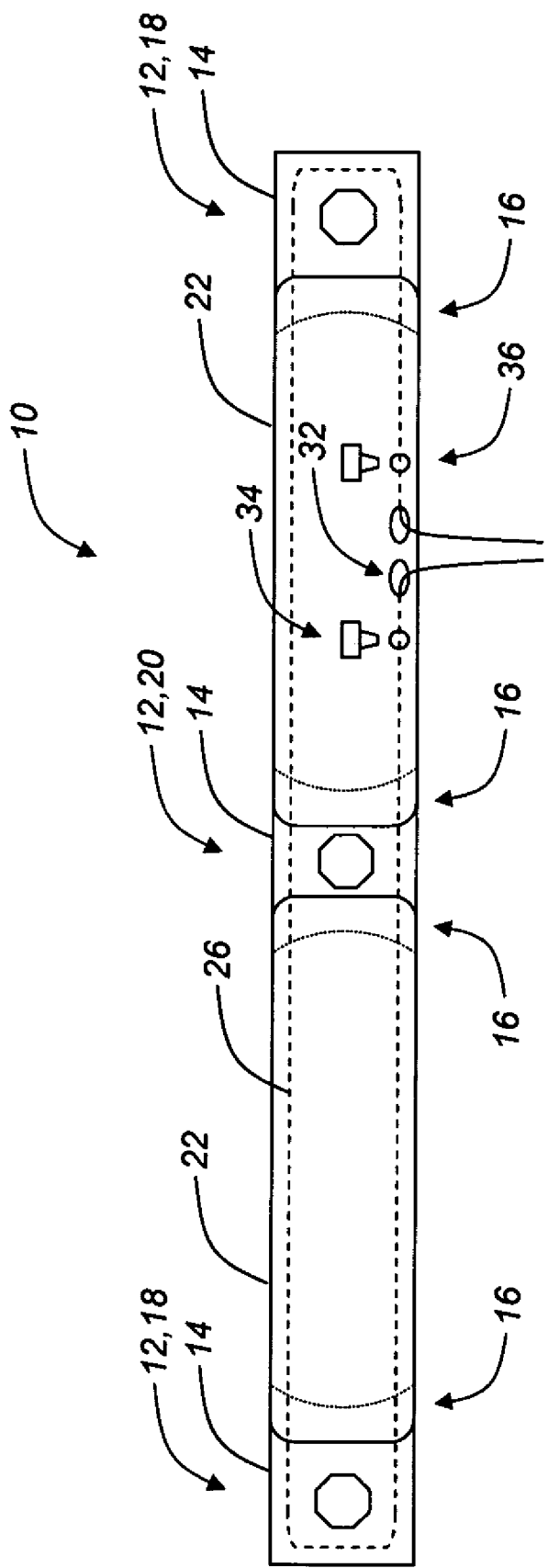
FIG. 2 is a top planar view illustrating the pedicle screw-based dynamic posterior stabilization system of FIG. 1.

FIGS. 1 and 2 are side and top planar views, respectively, illustrating one exemplary (multi-segment) embodiment of the pedicle screw-based dynamic posterior stabilization system of the present invention, the pedicle screw end portions being partially exploded from the stabilization bodies for clarity in FIG. 1. The pedicle screw-based dynamic posterior stabilization system 10 includes a plurality of pedicle screws 12 that are configured to be laterally inserted in either side of the facets of a plurality of adjacent vertebrae associated with a plurality of segments of the spine. It will be readily apparent to those of ordinary skill in the art that one or more segments can be stabilized using the pedicle screw-based dynamic posterior stabilization system 10, and that it is scalable in terms of the number of pedicle screws 12 or levels. Each of the pedicle screws 12 includes a head portion 14 that is configured to selectively receive a pedicle screw insertion device (i.e. a pedicle screw driver), and that forms one half of one "double-saddle" joint 16, in the case of the pedicle screw end portions 18, and one half of two "double-saddle" joints 16, in the case of the pedicle screw center portion 20. Each of the pedicle screws 12 is made of a substantially-rigid, medically-implantable metallic or non-metallic material, such as a titanium alloy or the like, well known to those of ordinary skill in the art. In general, each of the pedicle screws 12 has a head diameter or width of between about 10 mm and about 16 mm, a shaft diameter or width of between about 4.5 mm and about 7.5 mm, and an overall length of between about 30 mm and about 50 mm, although it will be readily apparent to those of ordinary skill in the art that other suitable dimensions can be used.

The pedicle screw-based dynamic posterior stabilization system 10 also includes a plurality of stabilization bodies 22 that are configured to be selectively disposed between the head portions 14 of the plurality of pedicle screws 12, the end portions of each of the stabilization bodies 22 forming the other half of one of the "double-saddle" joints 16 described above. Advantageously, these "double-saddle" joints allow the stabilization bodies 22 to pivot about the head portions 14 of the pedicle screws 12, as well as up and down with respect to the head portions 14 of the pedicle screws, providing the implanted pedicle screw-based dynamic posterior stabilization system 10 with improved ROM (at rest, in flexion, and in extension). Again, it will be readily apparent to those of ordinary skill in the art that one or more segments can be stabilized using the pedicle screw-based dynamic posterior stabilization system 10, and that it is scalable in terms of the number of stabilization bodies 22 or levels. Each of the stabilization bodies 22 is made of a substantially-rigid, medically-implantable metallic or non-metallic material, such as a PCU or the like, well known to those of ordinary skill in the art. In general, each of the stabilization bodies has diameter or width of between about 10 mm and about 16 mm and an overall length of between about 10 mm and about 50 mm, although it will be readily apparent to those of ordinary skill in the art that other suitable dimensions can be used.

Figure 3:
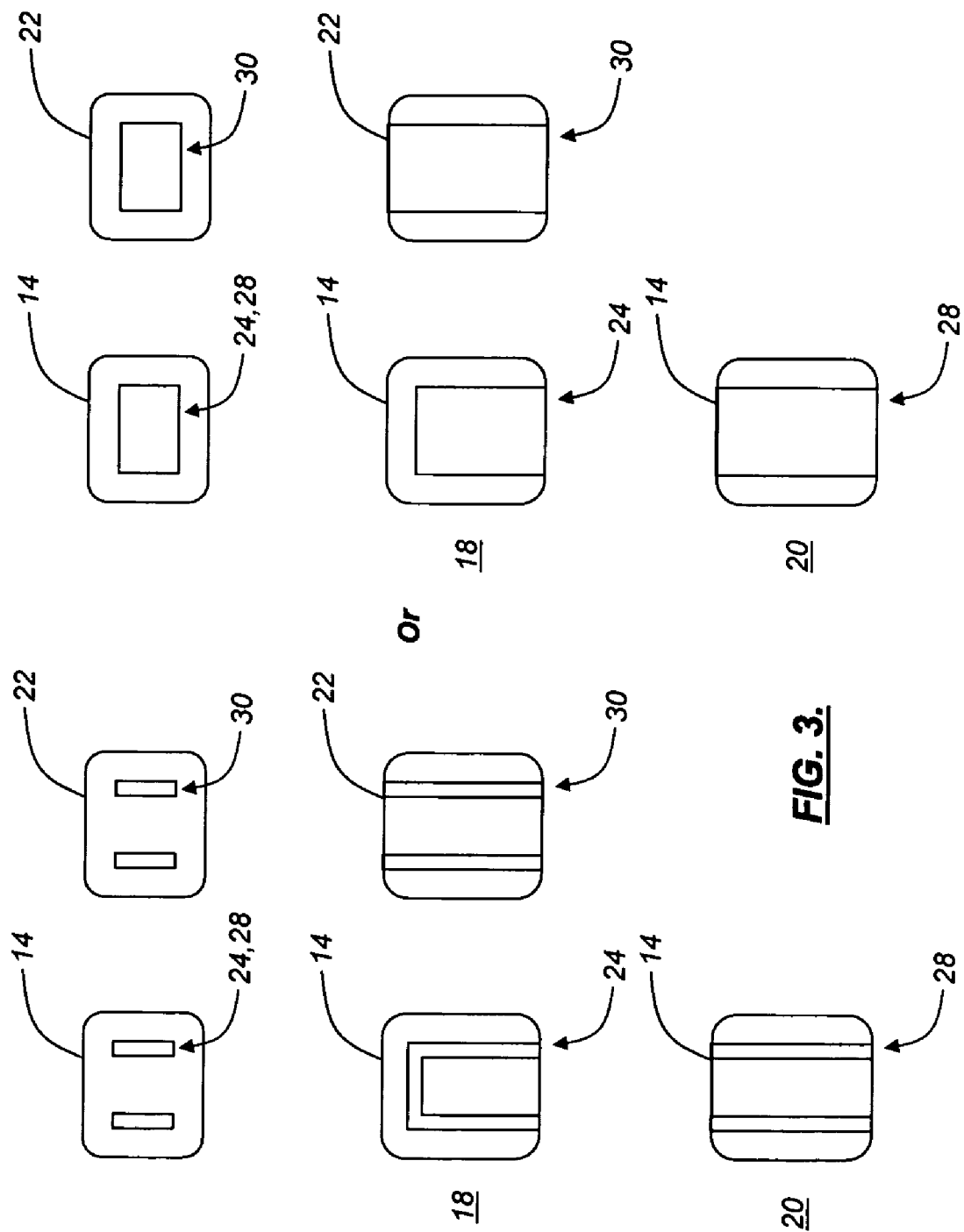
FIG. 3 is a plurality of side and top cross-sectional views of two exemplary embodiments of the head portions of the plurality of pedicle screws and the stabilization bodies of FIGS. 1 and 2, highlighting various band channel configurations.

FIG. 3 is a plurality of side and top cross-sectional views of two exemplary embodiments of the head portions of the plurality of pedicle screws and the stabilization bodies of FIGS. 1 and 2, highlighting various band channel configurations. Specifically, in the case of the pedicle screw end portions 18, the head portion 14 of each of the pedicle screws 12 includes a band channel 24 that is formed partially through the head portion 14. In one example, this band channel 24 comprises a substantially U-shaped hollow channel through which a band 26 (FIGS. 1 and 2), wire, or the like is selectively threaded, passing into and out of the head portion 14 of the pedicle screw 12 on the same side and securing a given pedicle screw 12 to a given stabilization body 22 (FIGS. 1 and 2), as described in greater detail herein below. In another example, the band channel 24 comprises a substantially cylindrical or rectangular hollow channel through which the band 26, wire, or the like is selectively threaded, again passing into and out of the head portion 14 of the pedicle screw 12 on the same side and securing a given pedicle screw 12 to a given stabilization body 22, as described in greater detail herein below. In the case of the pedicle screw center portion 20, the head portion 14 of the pedicle screw 12 includes a band channel 28 that is formed completely through the head portion 14. In one example, this band channel 28 comprises two substantially cylindrical or rectangular hollow channels through which the band 26, wire, or the like is selectively threaded, passing into and out of the head portion 14 of the pedicle screw 12 on opposite sides and securing a given pedicle screw 12 to a plurality of given stabilization bodies 22, as described in greater detail herein below. In another example, the band channel 28 comprises a substantially cylindrical or rectangular hollow channel through which the band 26, wire, or the like is selectively threaded, again passing into and out of the head portion 14 of the pedicle screw 12 on opposite sides and securing a given pedicle screw 12 to a plurality of given stabilization bodies 22, as described in greater detail herein below. In the case of the stabilization bodies 22, each of the stabilization bodies 22 includes a band channel 30 that is formed completely through the stabilization body 22. In one example, this band channel 30 comprises two substantially cylindrical or rectangular hollow channels through which the band 26, wire, or the like is selectively threaded, passing into and out of the stabilization body 22 on opposite sides and securing a given pedicle screw 12 to a given stabilization body or bodies 22, as described in greater detail herein below. In another example, the band channel 30 comprises a substantially cylindrical or rectangular hollow channel through which the band 26, wire, or the like is selectively threaded, again passing into and out of the stabilization body 22 on opposite sides and securing a given pedicle screw 12 to a given stabilization body or bodies 22, as described in greater detail herein below.

Referring again to FIGS. 1 and 2, as well as to FIG. 3, the band 26, wire, or the like is selectively threaded through the head portions 14 of two or more pedicle screws 12 and one or more stabilization bodies 22 such that the two or more pedicle screws 12 are movably secured to the one or more stabilization bodies 22. In order to accomplish this purpose, at least one of the one or more stabilization bodies 22 are formed with a plurality of ports 32 in communication with the band channels 24,28,30, one port forming an inlet port for the band 26, wire, or the like and another port forming an exit port for the band 26, wire, or the like. Once the band 26, wire, or the like has been threaded into the inlet port 26, through the band channel 30 of the stabilization body 22, through the band channel 24 of the head portion 14 of one pedicle screw 12, back through the band channel 30 of the stabilization body, through the band channel 24 of the head portion 14 of another pedicle screw 12, back through the band channel 30 of the stabilization body 22, and out of the outlet port 26, and once the band tension (and thus the frictional forces present in the "double-saddle" joints 16) has been adjusted as desired, a plurality of retention screws 34 or the like are inserted into a plurality of retention holes 36 disposed adjacent to the band 26, wire, or the like, thereby holding the band 26, wire, or the like secure in the band channels 24,28,30.

It should be noted that the "double-saddle" joints 16 of the present invention can be held together or formed via any other suitable mechanical means, provided that an adequate ROM with respect to the head portion 14 of the pedicle screws 12 and stabilization bodies 22 is maintained.

Figure 4:
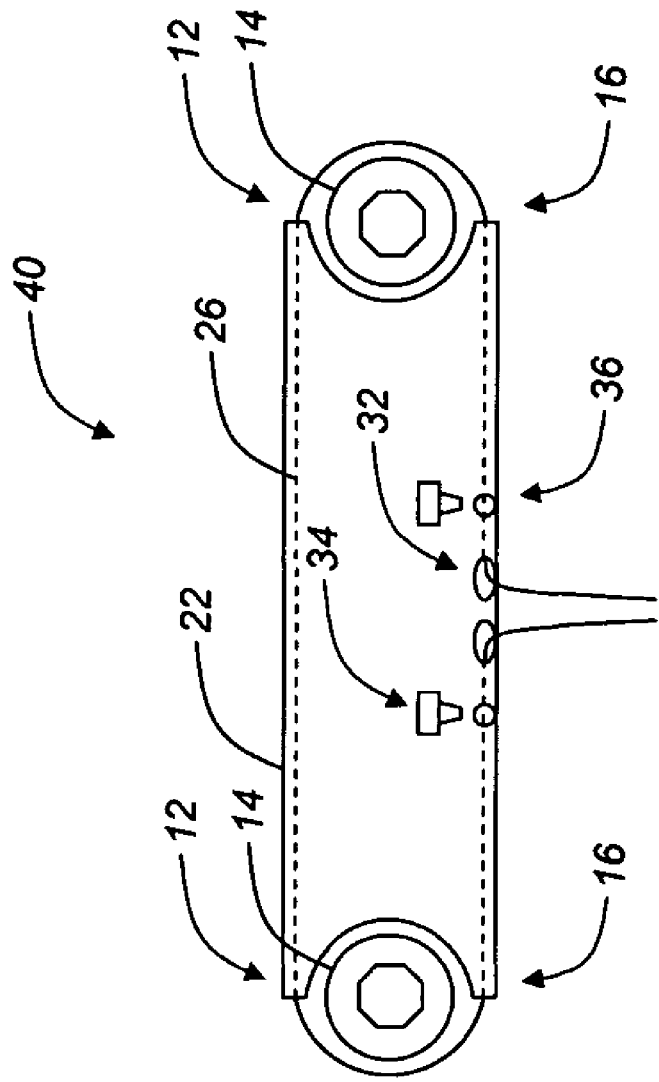
FIG. 4 is a top planar view illustrating another exemplary (single-segment) embodiment of the pedicle screw-based dynamic posterior stabilization system of the present invention.
Figure 5:
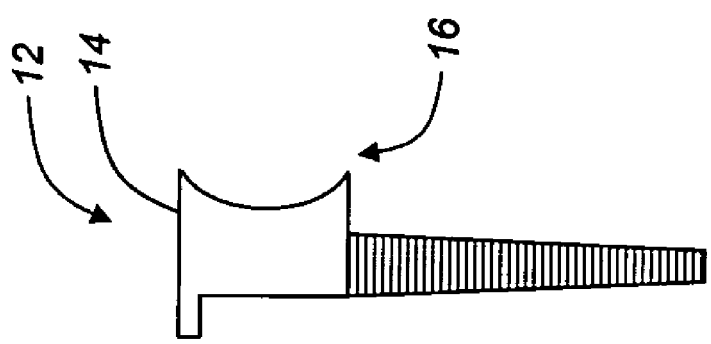
FIG. 5 is a top planar view illustrating one exemplary embodiment of the plurality of pedicle screws of FIG. 4.

FIG. 4 is a top planar view illustrating another exemplary (single-segment) embodiment of the pedicle screw-based dynamic posterior stabilization system of the present invention. The pedicle screw-based dynamic posterior stabilization system 40 includes a plurality of pedicle screws 12 that are configured to be laterally inserted in either side of the facets of a plurality of adjacent vertebrae associated with one segment of the spine. It will be readily apparent to those of ordinary skill in the art that one or more segments can be stabilized using the pedicle screw-based dynamic posterior stabilization system 40, and that it is scalable in terms of the number of pedicle screws 12 or levels. Referring to FIGS. 4 and 5, each of the pedicle screws 12 includes a head portion 14 that is configured to selectively receive a pedicle screw insertion device (i.e. a pedicle screw driver), and that forms one half of one "double-saddle" joint 16. Each of the pedicle screws 12 is made of a substantially-rigid, medically-implantable metallic or non-metallic material, such as a titanium alloy or the like, well known to those of ordinary skill in the art. In general, each of the pedicle screws 12 has a head diameter or width of between about 10 mm and about 16 mm, a shaft diameter or width of between about 4.5 mm and about 7.5 mm, and an overall length of between about 30 mm and about 50 mm, although it will be readily apparent to those of ordinary skill in the art that other suitable dimensions can be used.

The pedicle screw-based dynamic posterior stabilization system 40 also includes a stabilization body 22 that is configured to be selectively disposed between the head portions 14 of the plurality of pedicle screws 12, the end portions of the stabilization body 22 forming the other half of the "double-saddle" joints 16 described above. Advantageously, these "double-saddle" joints allow the stabilization body 22 to pivot about the head portions 14 of the pedicle screws 12, as well as up and down with respect to the head portions 14 of the pedicle screws, providing the implanted pedicle screw-based dynamic posterior stabilization system 40 with improved ROM (at rest, in flexion, and in extension). Again, it will be readily apparent to those of ordinary skill in the art that one or more segments can be stabilized using the pedicle screw-based dynamic posterior stabilization system 40, and that it is scalable in terms of the number of stabilization bodies 22 or levels. The stabilization body 22 is made of a substantially-rigid, medically-implantable metallic or non-metallic material, such as a PCU or the like, well known to those of ordinary skill in the art. In general, each of the stabilization bodies has diameter or width of between about 10 mm and about 16 mm and an overall length of between about 10 mm and about 50 mm, although it will be readily apparent to those of ordinary skill in the art that other suitable dimensions can be used.

The band 26, wire, or the like is selectively threaded through/around the head portions 14 of the plurality of pedicle screws 12 and the stabilization body 22 such that the plurality of pedicle screws 12 are movably secured to the stabilization body 22. In order to accomplish this purpose, the stabilization body 22 is formed with a plurality of ports 32 in communication with the band channels of the stabilization body 22 and the plurality of pedicle screws, one port forming an inlet port for the band 26, wire, or the like and another port forming an exit port for the band 26, wire, or the like. Once the band 26, wire, or the like has been threaded into the inlet port 26, through the band channel of the stabilization body 22, through the band channel of the head portion 14 of one pedicle screw 12, back through the band channel of the stabilization body, through the band channel of the head portion 14 of another pedicle screw 12, back through the band channel of the stabilization body 22, and out of the outlet port 26, and once the band tension (and thus the frictional forces present in the "double-saddle" joints 16) has been adjusted as desired, a plurality of retention screws 34 or the like are inserted into a plurality of retention holes 36 disposed adjacent to the band 26, wire, or the like, thereby holding the band 26, wire, or the like secure in the band channels.

Again, it should be noted that the "double-saddle" joints 16 of the present invention can be held together or formed via any other suitable mechanical means, provided that an adequate ROM with respect to the head portion 14 of the pedicle screws 12 and stabilization bodies 22 is maintained.

Although the present invention has been illustrated and described herein with reference to preferred embodiments and specific examples thereof, it will be readily apparent to those of ordinary skill in the art that other embodiments and examples may perform similar functions and/or achieve like results. All such equivalent embodiments and examples are within the spirit and scope of the present invention, are contemplated thereby, and are intended to be covered by the following claims.

What is claimed is:

1. A pedicle screw-based dynamic posterior stabilization system that is used to stabilize the segments of the cervical, thoracic, lumbar, and sacral spine as an adjunct to, or in place of, conventional spinal fusion using bone grafts, the system comprising:

a plurality of pedicle screws, each of the plurality of pedicle screws comprising a head portion, and the head portion of each of the plurality of pedicle screws forming a first portion of a joint, the first portion having a convex surface and a concave surface;

a substantially rigid stabilization body coupled to the plurality of pedicle screws, the stabilization body comprising a plurality of terminating end portions, each terminating end portion forming a second portion of a joint, wherein the second portion of a given joint is configured to pivot about a corresponding first portion on a first axis and on a second axis, the second portion having a convex surface and a concave surface, wherein the convex surface of the first portion mates with the concave surface of the second portion and the convex surface of the second portion mates with the concave surface of the first portion to form a double-hinged joint; and at least one of a substantially flexible or a substantially semi-rigid band spanning each joint and holding together the first portion and the second portion, wherein the band is disposed partially within the substantially rigid stabilization body, passes through at least one port manufactured into the substantially rigid stabilization body, and is disposed partially outside of the substantially rigid stabilization body where it is secured to the substantially rigid stabilization body.

2. The system of claim 1, wherein the head portion of each of the plurality of pedicle screws defines at least one hollow channel.

3. The system of claim 2, wherein the stabilization body defines at least one hollow channel.

4. The system of claim 3, wherein the band is threaded through the at least one hollow channel defined by the head portion of each of the plurality of pedicle screws and the at least one hollow channel defined by the stabilization body, the band selectively coupling the stabilization body to the plurality of pedicle screws.

5. The system of claim 3, wherein the stabilization body defines two hollow channels.

6. The system of claim 5, wherein the band is threaded through the at least one hollow channel defined by the head portion of each of the plurality of pedicle screws and the two hollow channels defined by the stabilization body, the band selectively coupling the stabilization body to the plurality of pedicle screws.

7. The system of claim 1, wherein the joints formed by the head portion of a pedicle screw and the terminating end of a stabilizing body provide relative rotation on two perpendicular axes.

8. A pedicle screw-based dynamic posterior stabilization method that is used to stabilize the segments of the cervical, thoracic, lumbar, and sacral spine as an adjunct to, or in place of, conventional spinal fusion using bone grafts, the method comprising:
    inserting a plurality of pedicle screws in the facets of a plurality of adjacent vertebrae of a spine, each of the plurality of pedicle screws comprising a head portion, and the head portion of each of the plurality of pedicle screws forming a first portion of a joint, the first portion having a convex surface and a concave surface;
    disposing a substantially rigid stabilization body between and coupling the stabilization body to the plurality of pedicle screws, the stabilization body comprising a plurality of terminating end portions, each terminating end portion forming a second portion of a joint, wherein the second portion of a given joint is configured to pivot about a corresponding first portion on a first axis and on a second axis, the first axis extending through the head portion of the pedicle screw and the second axis extending through the head portion of the pedicle screw and transverse to the first axis so that the second portion pivots about the head portion of the pedicle screw, the second portion having a convex surface and a concave surface, wherein the convex surface of the first portion mates with the concave surface of the second portion and the convex surface of the second portion mates with the concave surface of the first portion to form a double-hinged joint; and
    providing at least one of a substantially flexible or a substantially semi-rigid band spanning each joint and holding together the first portion and the second portion, wherein the band is disposed partially within the substantially rigid stabilization body, passes through at least one port manufactured into the substantially rigid stabilization body, and is disposed partially outside of the substantially rigid stabilization body where it is secured to the substantially rigid stabilization body.

9. The method of claim 8, wherein the head portion of each of the plurality of pedicle screws defines at least one hollow channel.

10. The method of claim 9, wherein the stabilization body defines at least one hollow channel.

11. The method of claim 10, wherein the band is threaded through the at least one hollow channel defined by the head portion of each of the plurality of pedicle screws and the at least one hollow channel defined by the stabilization body, the band selectively coupling the stabilization body to the plurality of pedicle screws.

12. The method of claim 10, wherein the stabilization body defines two hollow channels.

13. The method of claim 12, wherein the band is threaded through the at least one hollow channel defined by the head portion of each of the plurality of pedicle screws and the two hollow channels defined by the stabilization body, the band selectively coupling the stabilization body to the plurality of pedicle screws.

14. The method of claim 8, wherein the joints formed by the head portion of a pedicle screw and the terminating end of a stabilizing body provide relative rotation on two perpendicular axes.

15. A pedicle screw-based dynamic posterior stabilization system that is used to stabilize the segments of the cervical, thoracic, lumbar, and sacral spine as an adjunct to, or in place of, conventional spinal fusion using bone grafts, the system comprising:
    a plurality of pedicle screws, each of the plurality of pedicle screws comprising a head portion, and the head portion of each of the plurality of pedicle screws forming a first portion of a joint, the first portion having a convex surface and a concave surface that together form substantially the shape of a saddle;
    a substantially rigid stabilization body coupled to the plurality of pedicle screws, the stabilization body comprising a plurality of terminating end portions, each terminating end portion forming a second portion of a joint, wherein the second portion of a given joint is configured to pivot about a corresponding first portion, the second portion having a convex surface and a concave surface that together form substantially the shape of a saddle, wherein the convex surface of the first portion mates with the concave surface of the second portion and the convex surface of the second portion mates with the concave surface of the first portion to form a double-hinged joint; and
    at least one of a substantially flexible or a substantially semi-rigid band spanning each joint and holding together the first portion and the second portion, wherein the band is disposed partially within the substantially rigid stabilization body, passes through at least one port manufactured into the substantially rigid stabilization body, and is disposed partially outside of the substantially rigid stabilization body where it is secured to the substantially rigid stabilization body.

16. The system of claim 15, wherein the stabilization body defines at least one hollow channel.

17. The system of claim 16, wherein the band is threaded about the head portion of each of the plurality of pedicle screws and through the at least one hollow channel defined by the stabilization body, the band selectively coupling the stabilization body to the plurality of pedicle screws.

18. The system of claim 15, wherein the joints formed by the head portion of a pedicle screw and the terminating end of a stabilizing body provide relative rotation on two perpendicular axes.

19. A pedicle screw-based dynamic posterior stabilization method that is used to stabilize the segments of the cervical, thoracic, lumbar, and sacral spine as an adjunct to, or in place of, conventional spinal fusion using bone grafts, the method comprising:

inserting a plurality of pedicle screws in the facets of a plurality of adjacent vertebrae of a spine, each of the plurality of pedicle screws comprising a head portion, and the head portion of each of the plurality of pedicle screws forming a first portion of a joint, the first portion having a convex surface and a concave surface that together form substantially the shape of a saddle;

disposing a substantially rigid stabilization body between and coupling the stabilization body to the plurality of pedicle screws, the stabilization body comprising a plurality of terminating end portions, each terminating end portion forming a second portion of a joint, wherein the second portion of a given joint is configured to pivot relative to a corresponding first portion, the second portion having a convex surface and a concave surface that together form substantially the shape of a saddle, wherein the convex surface of the first portion mates with the concave surface of the second portion and the convex surface of the second portion mates with the concave surface of the first portion; and providing at least one of a substantially flexible or a substantially semi-rigid band spanning each joint and holding together the first portion and the second portion, wherein the band is disposed partially within the substantially rigid stabilization body, passes through at least one port manufactured into the substantially rigid stabilization body, and is disposed partially outside of the substantially rigid stabilization body where it is secured to the substantially rigid stabilization body.

20. The method of claim 19, wherein the stabilization body defines at least one hollow channel.

21. The method of claim 20, wherein the band is threaded about the head portion of each of the plurality of pedicle screws and through the at least one hollow channel defined by the stabilization body, the band selectively coupling the stabilization body to the plurality of pedicle screws.

22. The method of claim 19, wherein the joints formed by the head portion of the pedicle screw and the terminating end of a stabilizing body provide relative rotation on two perpendicular axes.

* * * * *